(12) United States Patent
Hatakeyama et al.

(10) Patent No.: US 6,676,901 B1
(45) Date of Patent: Jan. 13, 2004

(54) OXYGEN INDICATOR PACKAGE EQUIPPED WITH OXYGEN INDICATOR AND METHOD FOR MANUFACTURING THE SAME

(75) Inventors: Hidetoshi Hatakeyama, Tokyo (JP); Shigeo Tobari, Tokyo (JP); Shigeharu Iwauchi, Tokyo (JP); Masahiko Ohsawa, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 410 days.

(21) Appl. No.: 09/585,336

(22) Filed: Jun. 2, 2000

Related U.S. Application Data

(63) Continuation-in-part of application No. 09/172,256, filed on Oct. 14, 1998, now abandoned.

(30) Foreign Application Priority Data

Oct. 17, 1997 (JP) ............................................ 9-285667
Aug. 3, 1998 (JP) ........................................... 10-219450

(51) Int. Cl.[7] ............................................... G01N 33/00
(52) U.S. Cl. ................................ 422/58; 422/61; 436/1; 436/136; 436/166; 436/169; 73/23.2
(58) Field of Search ........................ 422/58, 61; 436/1, 436/136, 166, 169; 73/23.2; 426/232

(56) References Cited

U.S. PATENT DOCUMENTS 6,325,974 B1 * 12/2001 Ahvenainen et al. ....... 116/206

FOREIGN PATENT DOCUMENTS

JP          08-282740          1/1996

* cited by examiner

Primary Examiner—Lyle A. Alexander
(74) Attorney, Agent, or Firm—Nixon & Peabody, LLP

(57) ABSTRACT

The present invention provides an oxygen indicator comprising: an oxygen indicating agent including a substrate and an oxygen indicator composition fixed at the surface of the substrate; and a single-sided self-adhesive plastic member having a self-adhesive layer on one side thereof, wherein the oxygen indicating agent is provided over the single-sided sedlf-adhesive plastic member by causing the oxygen indicator composition to closely contact the self-adhesive layer. Moreover, this invention provides a deoxidizer package with an oxygen indicating function, to which the oxygen indicator is pasted. This invention further provides a method and apparatus for fixing the oxygen indicator to an object.

18 Claims, 7 Drawing Sheets

OXYGEN INDICATOR PACKAGE EQUIPPED WITH OXYGEN INDICATOR AND METHOD FOR MANUFACTURING THE SAME

This application is a continuation-in-part of U.S. Ser. No. 09/172,256 filed Oct. 14, 1998 now abandoned.

BACKGROUND OF THE INVENTION

1. Field of the Invention

The present invention relates to an oxygen indicator for indicating the presence or absence of oxygen by changes in color. More particularly, this invention relates to an adhesive oxygen indicator which is in a chip shape having a self-adhesive surface on one side and which is used by attaching the self-adhesive surface to a deoxidizer package or the inside of a packaging container. Moreover, this invention relates to a deoxidizer package with an oxygen indicating function, to which the oxygen indicator has been pasted. Furthermore, this invention relates to a method and apparatus for fixing the oxygen indicator to an object.

2. Description of the Related Art

An oxygen indicator detects changes in oxygen concentration within a packaging container for food or the like. Specifically, the oxygen indicator indicates by changing its color that the oxygen within a package has been removed sufficiently by a deoxidizer. Examples of proposed forms of such oxygen indicator are: products molded into tablets; products obtained by impregnating paper, threads, absorbent cotton, resin moldings, and other porous substances with solutions of oxygen indicator compositions; and products obtained by applying or printing oxygen indicator compositions on the surface of paper or film. Such oxygen indicators are widely used, either in the form as they are or in the state packaged in laminated plastic films, primarily for preserving the quality of foods by using deoxidizers. Moreover, methods or structures for fixing the aforementioned oxygen indicator to a deoxidizer package or to the inside of a packaging container with an adhesive or a double-sided adhesive tape have also been proposed and implemented because such methods or structures have advantageous effects, for example, that the risk of the oxygen indicator being eaten by mistake will be eliminated.

For example, Japanese Patent Laid-Open (Kokai) Publication No. SHO 64-66561 discloses an oxygen indicator provided with: an oxygen indicator layer on at least one side of synthetic paper; a transparent layer over the oxygen indicator layer; and an adhesive layer on the entire or a part of the front side and;/or back side thereof. Japanese Utility Model Laid-Open (Kokai) Publication No. HEI 4-3980 proposes a method for making an integrated form of an oxygen indicator by pasting a sheet-shaped oxygen indicating agent to a deoxidizer packaging material with an adhesive or a double-sided adhesive tape. With these pasted oxygen indicators, however, moisture or oil contained in foods or other preserved products sometimes penetrates into the oxygen indicating agent and impairs their color changing function.

Moreover, Japanese Patent Laid-Open (Kokai) Publication No. HEI 8-282740 discloses an integrated oxygen indicating agent in which the following layers are laminated in the order as listed as follows: a deoxidizer package, a double-sided adhesive tape, an oxygen indicator sheet, and transparent film. However, since this integrated oxygen indicator uses the double-sided adhesive tape, the following problems take place: the obtained product is expensive; the oxygen indicator becomes thick and inflexible, thereby causing a sense of a cumbersome existence; and the productivity for making the integrated form is low. In addition, since only the peripheral portions of the oxygen indicator sheet are bonded to a transparent film, when the oxygen indicator and the transparent film are cut, there is a possibility that moisture or oil permeates through the cut edges of the indicator sheet and transparent film into the entire oxygen indicator sheet, causing abnormal changes in the color of the sheet.

Furthermore, a study conducted by the inventors of the present invention revealed that when deoxidizers are used in the packaging container of foods or the like, changes in the color of the oxygen indicator often lag behind changes in the oxygen concentration inside the packaging container. This results in a problem that the color changes of the oxygen indicator do not correspond to the changes in oxygen concentration.

A deoxidizer package is manufactured usually by packaging a deoxidizer with a packaging material having heat-sealability by means of heat sealing such as three-side sealing or four-side sealing. The deoxidizer package exhibits a function to absorb oxygen within a container and is used to maintain the freshness of foods packaged and to preserve pharmaceuticals. A deoxidizer package with an oxygen indicating function is also introduced, which is provided with the aforementioned oxygen indicator. This deoxidizer package with the oxygen indicating function is practically used as a product obtained by fixing a label-, sheet-, thread-, or plate-type oxygen indicator tape to the deoxidizer package with an adhesive or a double-sided adhesive tape.

Japanese Patent Laid-Open (Kokai) Publication No. HEI 8-275760 discloses a deoxidizer package with an oxygen indicating function, concerning which a thread-shaped oxygen indicator covered with a transparent adhesive tape is bonded to peripheral seal portions of the deoxidizer package, thereby it is possible to confirm color changes from any side, either front or back, of the deoxidizer package. However, since the edges of this integrated oxygen indicator are open, there is a problem in that moisture or oil contained in a preserved product such as foods penetrates into the thread-shaped oxygen indicator, thereby impairing the color changing function. Also, there is a problem in that loosen threads attach to the foods.

SUMMARY OF THE INVENTION

It is an object of the present invention to solve the above-described problems of the conventional oxygen indicators such as water/oil resistance and thickness as well as the cost problem, and to develop an adhesive oxygen indicator that has a wide range of uses and exhibits excellent color changing performance. Specifically, it is an object of this invention to provide an adhesive oxygen indicator that changes its color rapidly in response to changes in oxygen concentration, and to provide products in which this oxygen indicator is used. It is a still another object to solve the aforementioned problems and to provide a method and apparatus for fixing the new adhesive oxygen indicator as described above to objects such as deoxidizer packages, packaging pouches, small-pouch packages, packaging boxes, packaging cases, and packaged goods.

Furthermore, it is an object of this invention to develop a deoxidizer package with an oxygen indicating function, which can solve the aforementioned problems, which can be applied for a wide range of practical uses, which has excellent performance and safety, and which enables users to see the color changes of the oxygen indicator from either side of the deoxidizer package.

In order to achieve the above-described objects, this invention provides an oxygen indicator comprising:

an oxygen indicating agent including a substrate and an oxygen indicator composition fixed at the surface of the substrate; and a single-sided self-adhesive plastic member having a self-adhesive layer on one side thereof, wherein the oxygen indicating agent is provided over the single-sided self-adhesive plastic member by causing the oxygen indicator composition to closely contact the self-adhesive layer.

The single-sided self-adhesive plastic member is limitedly permeable to gas and moisture, and the single-sided self-adhesive plastic member is at least partly transparent. Furthermore, the width of the single-sided self-adhesive plastic member can be wider than that of the oxygen indicating agent and the oxygen indicating agent can be provided at an approximate center position in the width direction of the single-sided self-adhesive plastic member.

It is possible to employ such structure that the oxygen indicator composition is fixed at the surface of the substrate by means of application, printing, or impregnation.

The substrate and the single-sided self-adhesive plastic member can be formed in a strip shape, and a plurality of the oxygen indicator compositions can be fixed at regular intervals to the surface of the substrate and the respective oxygen indicator compositions can be made to closely contact the self-adhesive layer, thereby the respective oxygen indicating agents can be provided on the strip-shaped single-sided self-adhesive plastic member.

Moreover, a release member can be placed on the side of the single-sided self-adhesive plastic member where the self-adhesive layer is not provided.

Furthermore, the oxygen indicator of this invention can be used in the state of being cut into appropriate lengths.

The self-adhesive layer can be provided on the back side of the substrate and a release member can be provided thereon through the intermediary of the self-adhesive layer. This release member can be composed of release paper.

This invention also provides an oxygen indicator web comprising:

a plurality of oxygen indicators described above; and a release member with the plurality of oxygen indicators provided thereon, wherein the plurality of oxygen indicators are provided at regular intervals on the release member through the intermediary of the self-adhesive layer.

This invention provides a deoxidizer package with an oxygen indicating function, wherein the oxygen indicator described above is provided at a deoxidizer package containing a deoxidizer in a packaging material.

This invention also provides a deoxidizer package with an oxygen indicating function, wherein the above-described oxygen indicator web is provided at a deoxidizer package containing a deoxidizer in a packaging material.

The deoxidizer package is obtained by sealing at least a part of the packaging material containing the deoxidizer, and the oxygen indicator can be provided in the state of being held in the sealed portion. The oxygen indicator can be seen from either side of the deoxidizer package. Both sides of the deoxidizer package can be permeable to gas.

Moreover, this invention provides a method for manufacturing a deoxidizer package with an oxygen indicating function, comprising the steps of:

pasting the above-described oxygen indicator continuously to a packaged deoxidizer strip where a plurality of deoxidizer packages, which contain deoxidizers in packaging materials, are placed continuously, thereby forming a strip-shaped deoxidizer package with an oxygen indicating function; and cutting the strip-shaped deoxidizer package with the oxygen indicating function to separate the continuous deoxidizer packages of the strip-shaped deoxidizer package with the oxygen indicating function into individual units.

This invention also provides a method for manufacturing a deoxidizer package with an oxygen indicating function, comprising the steps of:

pasting the above-described oxygen indicator web continuously to a packaged deoxidizer strip where a plurality of deoxidizer packages, which contain deoxidizers in packaging materials, are placed continuously, thereby forming a strip-shaped deoxidizer package with an oxygen indicating function; and cutting the strip-shaped deoxidizer package with the oxygen indicating function to separate the continuous deoxidizer packages of the strip-shaped deoxidizer package with the oxygen indicating function into individual units.

Moreover, this invention provides a packaging IS container equipped with an oxygen indicator, wherein the above-described oxygen indicator is pasted to the interior of the packaging container.

Furthermore, this invention provides a method for fixing the above-described oxygen indicator to a strip-shaped object, wherein a self-adhesive tape, which has a self-adhesive layer formed thereon and which is at least partially transparent, is pasted to the strip-shaped object in a manner such that the oxygen indicator is interposed between this object and the self-adhesive tape.

This invention further provides a method for fixing, to a packaged deoxidizer strip where a plurality of deoxidizer packages containing deoxidizers are placed continuously, a tape-shaped oxygen indicator which comprises a tape-shaped oxygen indicating agent obtained by fixing an oxygen indicator composition to a tape-shaped substrate, and a single-sided self-adhesive plastic tape that is wider than the tape-shaped oxygen indicating agent, that is at least partially transparent, and that is provided with a self-adhesive layer on one side thereof, the tape-shaped oxygen indicating agent being adhesively attached to the approximate center (in the width direction) of the single-sided self-adhesive plastic tape, wherein the parts of the single-sided self-adhesive plastic tape, which are devoid of the tape-shaped oxygen indicating agent, are pasted and fixed to the packaged deoxidizer strip.

This invention also provides a method for fixing, to a packaged deoxidizer strip where a plurality of deoxidizer packages containing deoxidizers are placed continuously, a tape-shaped oxygen indicator which comprises a tape-shaped oxygen indicating agent obtained by fixing an oxygen indicator composition to a tape-shaped substrate, and a single-sided self-adhesive plastic tape that is wider than the tape-shaped oxygen indicating agent, that is at least partially transparent, and that is provided with a self-adhesive layer on one side thereof, the tape-shaped oxygen indicating agent being adhesively attached to the approximate center (in the width direction) of the single-sided self-adhesive plastic tape, wherein the method for fixing the tape-shaped oxygen indicator comprises the steps of:

interposing the tape-shaped oxygen indicating agent between the single-sided self-adhesive plastic tape and the packaged deoxidizer strip; and pasting the self-adhesive layer of the single-sided self-adhesive plastic tape to the packaged deoxidizer strip, thereby pasting and fixing the interposed tape-shaped oxygen indicating agent to the packaged deoxidizer strip.

This invention also provides a fixing apparatus comprising:

a device for delivering a packaged deoxidizer strip where a plurality of deoxidizer packages containing deoxidizers are placed continuously;

a device for delivering a tape-shaped oxygen indicating agent, which is obtained by fixing an oxygen indicator composition to a tape-shaped substrate, toward the packaged deoxidizer strip;

a device for delivering a transparent film having a self-adhesive layer formed on one side thereof toward the packaged deoxidizer strip; and a device for pasting the self-adhesive layer of the transparent film to the packaged deoxidizer strip in a manner such that the tape-shaped oxygen indicating agent is interposed between the packaged deoxidizer strip and the transparent film.

This invention further provides an apparatus for fixing, to a packaged deoxidizer strip where a plurality of deoxidizer packages containing deoxidizers are placed continuously, a tape-shaped oxygen indicator which comprises a tape-shaped oxygen indicating agent obtained by fixing an oxygen indicator composition to a tape-shaped substrate, and a single-sided self-adhesive plastic tape that is at least partially transparent and that is provided with a self-adhesive layer on one side thereof, the tape-shaped oxygen indicating agent being directly attached to the single-sided self-adhesive plastic tape, wherein the apparatus for fixing the tape-shaped oxygen indicator comprises: a device for continuously delivering the packaged deoxidizer strip; a device for continuously delivering the tape-shaped oxygen indicating agent toward the packaged deoxidizer strip; a device for delivering the single-sided self-adhesive plastic tape toward the packaged deoxidizer strip; and a device for pasting the self-adhesive layer of the single-sided self-adhesive plastic tape to the packaged deoxidizer strip in a manner such that the tape-shaped oxygen indicating agent is interposed between the single-sided self-adhesive plastic tape and the packaged deoxidizer strip.

Concerning this fixing apparatus, the single-sided self-adhesive plastic tape is wider than the tape-shaped oxygen indicating agent, and the device for pasting the self-adhesive layer of the single-sided self-adhesive plastic tape to the packaged deoxidizer strip is configured in a manner such that on the surface of the single-sided self-adhesive plastic tape where the self-adhesive layer thereof is formed, both side margins (in the width direction) of the single-sided self-adhesive plastic tape constitute the parts devoid of the tape-shaped oxygen indicating agent so that the tape-shaped oxygen indicating agent is located in the approximate center (in the width direction) of the single-sided self-adhesive plastic tape, and such parts devoid of the, tape-shaped oxygen indicating agent can be pasted to the packaged deoxidizer strip.

Alternatively, a self adhesive layer is provided on the back side of the substrate and a release member is provided on the self-adhesive layer. In this case, the oxygen indicator can be fixed to the deoxidizer package through the intermediary of, the self-adhesive layer.

The above-described oxygen indicating agent can be obtained by applying or printing a plurality of oxygen indicator compositions, either at regular intervals or continuously, on one side of a limitedly moisture-permeable plastic film or synthetic paper.

Concerning the above-described method, the object can be composed of a packaged deoxidizer strip where a plurality of deoxidizer packages containing deoxidizers are placed continuously, and the above-described method can further comprise the step of pasting the oxygen indicating agent and the self-adhesive tape to the packaged deoxidizer strip and then cutting the obtained strip to separate the respective deoxidizer packages into individual units.

Concerning the above-described apparatus, the object can be composed of a packaged deoxidizer strip where a plurality of deoxidizer packages containing deoxidizers are placed continuously, and the apparatus can further comprise the device of pasting the oxygen indicating agent and the self-adhesive tape to the packaged deoxidizer strip and then cutting the obtained strip to separate the respective deoxidizer packages into individual units.

The term "tape shape" used in relation to this invention refers to the shape of which length is greater than its width and of which thickness is less than its width. The oxygen indicator of this invention should have a thickness of 2 mm or less, more preferably 0.5 mm or less, and should have a width ranging from 3 mm to 30 mm. Although the length of the oxygen indicator is not specifically limited because it can be cut in an appropriate size at the time of pasting and then be used, it is desirable that the length of the oxygen indicator be at least several tens of meters, which will enable continuous processing, in order to minimize the costs for manufacturing and,for the use of the oxygen indicator.

The oxygen indicator of this invention has a very simple structure which basically comprises an oxygen indicating agent and a single-sided self-adhesive plastic tape. Accordingly, the productivity is high and it is possible to reduce the costs. In addition, the operability at the time of use is high, thereby making it possible to reduce the total costs required for the oxygen indicator.

Moreover, the single-sided self-adhesive tape adopts a reasonable layer structure such that the oxygen indicator composition surface of the oxygen indicating agent is sealed in the approximate central portion of the single-sided self-adhesive tape and the margin portions of the tape edges are used for adhesive attachment and pasting. Accordingly, the resultant oxygen indicator of this invention is thin and highly flexible, has excellent color changing performance and water and oil resistance as an oxygen indicator, and exhibits good oxygen indicating performance without suffering deterioration in performance even under the rigorous working conditions of high humidity. Because of its excellent flexibility, the oxygen indicator can exhibit its adherence capability to uneven or low-rigidity surfaces of deoxidizer packages or food-containing packaging containers.

When the oxygen indicator of this invention is used, one surface of the oxygen indicator composition is covered with the single-sided self-adhesive tape, and the opposite surface is separated and hermetically sealed by the substrate from the outside atmosphere. However, as compared with a conventional type of oxygen indicator of which oxygen indicator composition is exposed to the outside atmosphere, the oxygen indicator of this invention shows a higher color change rate in response to a decrease in the oxygen concentration within the outside atmosphere. Although the mechanism of this phenomenon is not yet clear, it might be attributed to the fact that the single-sided self-adhesive tape prevents excessive absorption of moisture (which causes deterioration of the oxygen indicating performance) and has a function of adequately transmitting the atmospheric: gas, and that the oxygen indicator composition is sealed without leaving any void, thereby preventing the oxygen indicator components from transferring to the outside.

The oxygen indicating agent of this invention is made by pasting the oxygen indicator composition to the substrate and indicates the existence or absence of oxygen as the oxygen indicator composition changes its color according to the oxygen concentration in the ambient atmosphere.

As the oxygen indicator composition, compositions containing the following substances as essential components are preferably used: dyes which show color changes with a reducing agent such as anthraquinone dye, indigo dye, or thiazine dye, or sulfur dye; alkali substances such as hydroxides or salts of alkali metals or alkaline earth metals; and reducing agents: such as reducing sugar. In addition to these essential components, a solvent, a dye or pigment which does not change color even with the existence of the reducing agent, a water soluble high polymer, a binder resin, and other substances are combined and added as necessary, and the obtained composition is then attached to the tape-shaped substrate. Examples of the method of attachment include application, printing, and impregnation.

As for the label-shaped oxygen indicating agent, in order to exhibit high oxygen indicating performance even under severe conditions of high humidity, such oxygen indicating agent is preferably used that is obtained by applying or printing the oxygen indicator composition onto one side of limitedly gas- and moisture-permeable synthetic paper or film.

A limitedly gas- and moisture-permeable synthetic paper or film is used as the substrate. Examples of such materials include polyethylene, polypropylene, polyester, polyamide, polycarbonate, cellulose acetate, and cellophane. Oriented polypropylene or polyester is preferred from the standpoint of transparency, flexibility, strength, and the like. No particular limitations are imposed on the thickness of the substrate as long as practical strength and flexibility are obtained, but a thickness of 10–100 microns is preferred. In addition, the oxygen permeability of the label substrate should preferably be 50–3000 $cc/m^2 \cdot day \cdot atm$, and moisture permeability should preferably be 50 $g/m^2 \cdot day$ or lower.

It is desirable that this substrate be opaque or be appropriately colored in order to make the color changes of the oxygen indicating agent more visible. Moreover, it is possible to leave a part of the substrate transparent so that the color changes of the oxygen indicator can be observed, while using the remaining parts for displaying information such as characters or pictorial symbols for concealment, and it is also possible to print the substrate with an appropriate color in order to make it easier to distinguish the color of the oxygen indicating agent.

The oxygen indicating agent on the substrate should be so large that it is visible from either side of the deoxidizer package, when the oxygen indicator is pasted in a manner that the oxygen indicator encloses the seal portion of the deoxidizer package. Specifically, the oxygen indicating agent on the substrate forms a continuous or continual belt shape of the width of more than 2 mm, preferably 4–20 mm, or a circle or oval shape of the diameter of more than 2 mm, preferably 4–20 mm.

The single-sided self adhesive tape as described above is obtained preferably by applying or laminating an adhesive over one side of a plastic film. Examples of materials for the plastic film include polyethylene, polypropylene, polyester, polyamide, polycarbonate, cellulose acetate, and cellophane. Polypropylene, polyester or polyamide is preferred. Oriented polypropylene or polyester is more preferred from the standpoint of transparency, flexibility, and strength. No particular limitations are imposed on the thickness of the plastic film as long as practical strength and flexibility are obtained, but a thickness of 10–100 microns is preferred. The plastic film may either be colorless and transparent or be appropriately colored and transparent in order to make the color changes of the oxygen indicating agent more visible. Moreover, it is possible to leave a part of the plastic film transparent so that the color changes of the oxygen indicating agent can be observed, while using the remaining parts of the plastic film for displaying information such as characters or pictorial symbols for concealment, and it is also possible to print the plastic film with an appropriate color in order to make it easier to distinguish the color of the oxygen indicating agent. In addition, the oxygen permeability of the plastic film should preferably be 50–3000 $cc/m^2 \cdot day \cdot atm$, and moisture permeability should preferably be 50 $g/m^2 \cdot day$ or lower.

As examples of materials composing the self-adhesive layer, the following materials can be used: synthetic rubbers, natural rubbers, acrylics, silicones, and other known materials. It is desirable that the self-adhesive layer be applied to or laminated over the entire surface of one side of the plastic film. In this case, the type and thickness of the self-adhesive layer may be selected as appropriate in consideration of the following points that the pigment used for the oxygen indicating agent will not stain or the color changes of the pigment will not be inhibited, that the self-adhesive layer should have excellent transparency, that the self-adhesive layer should be highly stable and hygienic, and that appropriate adhesion to an adherend should be achieved.

This self-adhesive layer can be formed by various methods, including: a method of applying an adhesive as an emulsion or a solution diluted with a solvent to a base, which composes the single-sided self-adhesive plastic tape, and then drying the applied adhesive; a method of extruding and laminating an adhesive to the base; and a method of transferring an adhesive, which has been formed in a film shape, from release paper to the base.

This invention realizes better water and oil resistance by covering the oxygen indicator composition with the single-sided self-adhesive plastic tape which is limitedly permeable to gas and moisture and is transparent. Accordingly, it is desirable that the entire oxygen indicator composition be in direct contact with the self-adhesive layer substantially without leaving any void or the substantially entire adhesive surface of the oxygen indicating agent is sealed by the self-adhesive tape.

The oxygen indicator of this invention can be made in a label which is thin and in a chip shape. Accordingly, such oxygen indicator will hardly decrease the capabilities of a deoxidizer and it will not cause any sense of a cumbersome existence when integrated with a deoxidizer. In addition, since the oxygen indicator has the self-adhesive surface on the back side, it hardly comes off. Since the oxygen indicator is covered!with the single-sided self-adhesive plastic tape which is limitedly permeable to gas and moisture and is transparent, the oxygen indicator is resistant to water and oil.

Moreover, a plurality of the oxygen indicators of this invention can be formed into a web where the oxygen indicators are pasted with their self-adhesive surfaces on their back sides to release paper, the oxygen indicator can be readily used for pasting when it is peeled off from the release paper. Therefore, manufacturing costs are reduced and high-speed pasting can be performed by using an automatic pasting machine, thereby improving the productivity.

DETAILED DESCRIPTION OF THE PREFERRED EMBODIMENTS

EMBODIMENT 1

Figure 1:
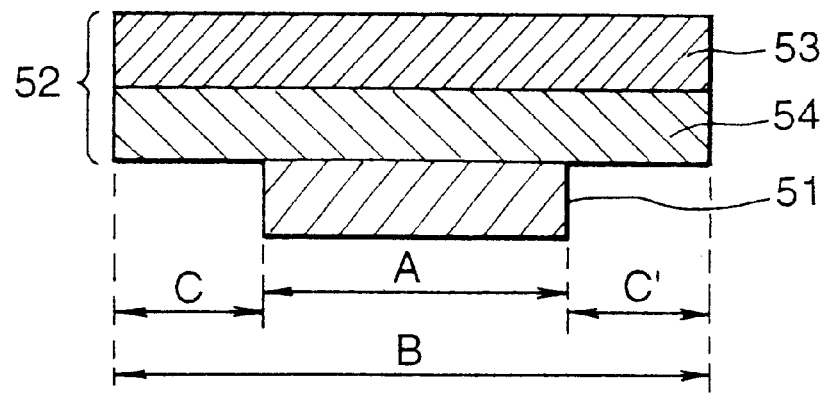
FIG. 1 is a cross-sectional view of an example of the tape-shaped oxygen indicator of this invention.

FIG. 1 is a cross-sectional view of an oxygen indicator according to Embodiment 1 as taken in the width direction thereof. Reference numeral 51 indicates a tape-shaped oxygen indicating agent, and reference numeral 52 indicates a single-sided self-adhesive plastic tape. The single-sided self-adhesive tape 52 is obtained by applying or laminating an adhesive 54 over the entire surface of one side of a plastic film 53. A tape-shaped oxygen indicating agent 51 of which width A is less than width B of the single-sided self-adhesive tape 52 is fixed to the single-sided self-adhesive tape 52 with the aid of the adhesive 54 in the approximate center (in the width direction) of the single-sided self-adhesive tape 52. Because width A is less than width B, peripheral adhesive portions C and C' are exposed on both sides of the tape-shaped oxygen indicating agent 51, and these portions are pasted to an object such as a deoxidizer package. There is no need for C and C' to have the same dimensions as long as their adhering capability to an object will not be lost.

The single-sided self-adhesive plastic tape thus obtained may have any width as long as it exceeds width A of the tape-shaped oxygen indicating agent 51 and can provide the necessary width for C and C' shown in FIG. 1, but a width of 3–50 mm is preferred, and more preferably about 5–30 mm, from the viewpoint of ease of handling and cost. In addition, it is desirable that the width of C and C' in FIG. 1 be about 1–5 mm each. In addition, in order to enable smooth unrolling, with little resistance, of the single-sided self-adhesive tape 52 rolled around a paper tube or core, it is desirable that a release agent such as silicone or alkyd resin be applied to the side where the adhesive is not provided.

The plastic film may either be colorless and transparent or be appropriately colored in order to make the color changes of the oxygen indicating agent more visible. Moreover, it is possible to leave a part of the plastic film transparent so that the color changes of the oxygen indicating agent can be observed, while using the remaining parts of the plastic film for displaying information such as characters or pictorial symbols for concealment, and it is also possible to print the plastic film with an appropriate color in order to make it easier to distinguish the color of the oxygen indicating agent.

The width of the tape-shaped oxygen indicating agent should be about 1–20 mm, preferably about 2–15 mm. An excessively narrow tape is difficult to see, while an excessively wide tape is expensive and difficult to handle. In addition, the thickness of the tape-shaped oxygen indicating agent 51 should preferably be 1 mm or less, and more preferably 0.5 mm or less, to ensure flexibility and aesthetic appeal.

Figure 2:
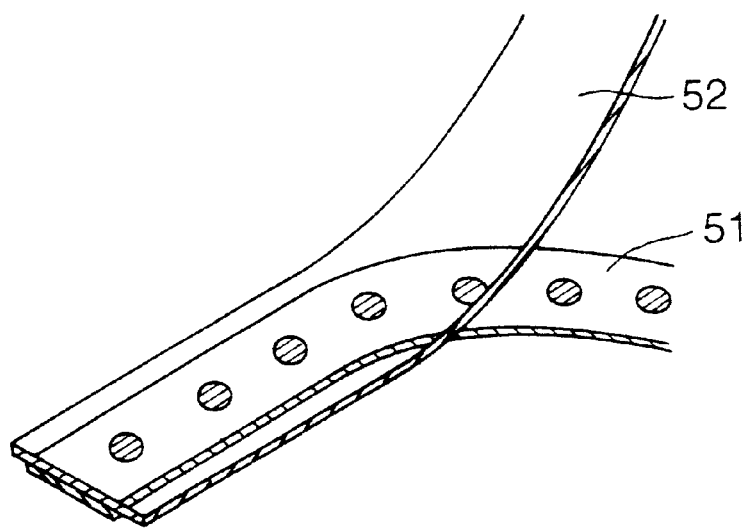
FIG. 2 is a schematic depicting an example of a part of the step of manufacturing the tape-shaped oxygen indicator of this invention.
Figure 3:
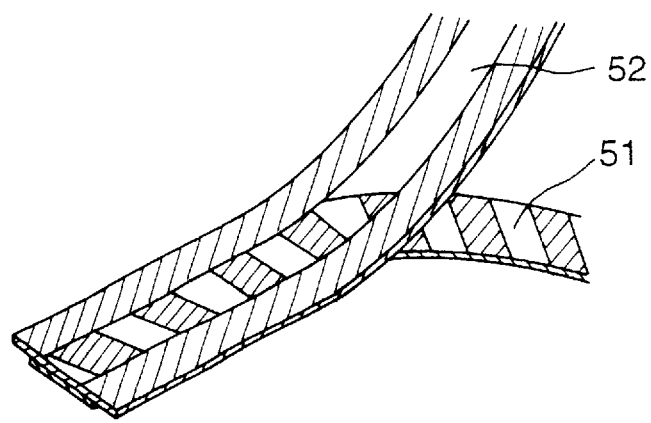
FIG. 3 is a schematic depicting an example of a part of the step of manufacturing the tape-shaped oxygen indicator of this invention.
Figure 4:
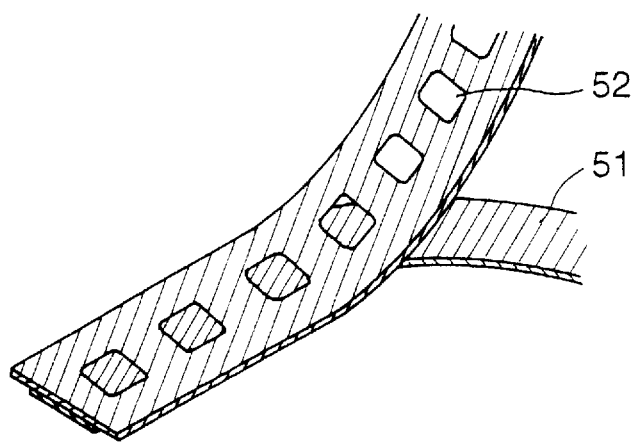
FIG. 4 is a schematic depicting an example of a part of the step of manufacturing the tape-shaped oxygen indicator of this invention.

When the tape-shaped oxygen indicating agent 51 is combined with the single-sided self-adhesive plastic tape 52, a color change portion (oxygen indicator composition) can be formed continuously in the lengthwise direction of the tape. However, in order to make it easier to distinguish the color changes, it is desirable that the color change portion and a color unchangeable portion be placed alternately in the lengthwise direction of the tape. Preferred patterns are exemplified in FIGS. 2–4. FIG. 2 depicts a combination of the single-sided self-adhesive tape that is transparent across its entire surface and the tape-shaped oxygen indicating agent on which dots of an oxygen indicator composition are placed continuously. FIG. 3 depicts a combination of the single-sided self-adhesive tape having a transparent portion that extends continuously in the lengthwise direction, and the tape-shape oxygen indicating agent on which the oxygen indicator composition is arranged in stripes. FIG. 4 depicts a combination of the single-sided self-adhesive tape having transparent portions that are arranged intermittently in the lengthwise direction, and the tape-shaped oxygen indicating agent on which the 4 oxygen indicator composition is placed across the entire surface. However, this invention is not limited to the above-described examples.

The strip-shaped oxygen indicator of this invention is obtained by adhesively attaching the oxygen indicating agent to the approximate center (in the width direction) of the single-sided self-adhesive tape in a manner such that the oxygen indicator composition surface closely contacts the self-adhesive layer. The oxygen indicator is in a form, for example, where the tape which is at least several tens of meters long is rolled around a paper tube. The term "approximate center in the width direction" refers to a position that affords sufficient width for allowing C and C' in FIG. 1 to be pasted to an object (adherend) with sufficient adhesive force. Since the self-adhesive layer is formed over almost the entire surface of the adhesive surface of the single-sided self-adhesive tape, the oxygen indicator composition surface of the oxygen indicating agent is adhesively attached to the self-adhesive layer of the single-sided self-adhesive tape in a substantially void-free manner. The presence of voids between the oxygen indicator composition surface and the self-adhesive layer of the single-sided self-adhesive tape due to the absence of adhesive attachment between them sometimes causes changes in the color of the oxygen indicating agent to lag behind decrease of the oxygen concentration inside a packaging container when food or the like is packaged and preserved by using a deoxidizer.

Alternatively, an adhesive is applied on the surface of the substrate where the ink is not applied, thereby forming an self-adhesive layer, to which release paper is then attached. To the surface of the substrate where the ink is applied, a transparent single-sided self-adhesive tape, which is coated with an adhesive on the entire surface of one side thereof, is attached. Then, the lamination obtained above is cut, while the release paper is left uncut, thereby obtaining a label-shaped oxygen indicator of which peripheral portions are removed and which are pasted to the release paper, thereby obtaining an oxygen indicator strip where oxygen indicators are arranged in a line at regular intervals over the release paper.

This strip-shaped oxygen indicator is cut into appropriate lengths to obtain individual adhesive oxygen indicators, which are used by being pasted to packaging materials or deoxidizers for the purpose of, for example, packaging foods in the deoxidized state.

As another example of use, long strips of the strip-shaped oxygen indicating agent and the single-sided self-adhesive tape, each with a length of at least several tens of meters, can be rolled up respectively, and be then unrolled simultaneously to place them one over another, and immediately after such lamination the obtained laminated strips can be used by being pasted to an object.

In particular, a deoxidizer package with the oxygen indicator pasted thereon can be used conveniently for the packaging of foods in the deoxidized state. As a method for manufacturing the deoxidizer package with the oxygen indicator pasted thereon, it is inexpensive and reasonable to adopt the method of continuously pasting together the strip-shaped adhesive oxygen indicating agent and a packaged deoxidizer strip, and then cutting the obtained packaged deoxidizer strip in the pasted state into individual units.

It is also possible to directly paste the oxygen indicating agent to the interior of a packaging container, thereby forming the packaging container equipped with the oxygen indicator. For example, the oxygen indicator may be pasted to a tray, partition, or other structural element or packaging material inside the packaging container, allowing the oxygen indicator to be visible from the single-sided self-adhesive tape side.

Figure 5:
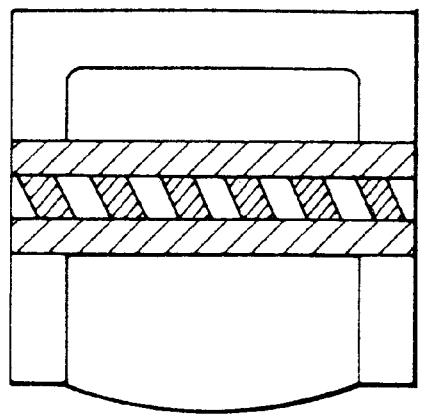
FIG. 5 is a plan view depicting an example of a deoxidizer package to which, the oxygen indicator of this invention has been pasted.
Figure 6:
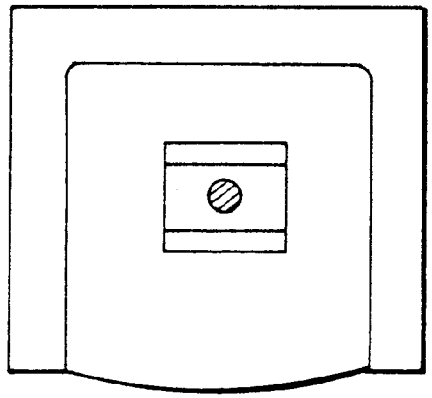
FIG. 6 is a plan view depicting an example of a deoxidizer package to which [1]the oxygen indicator of this invention has been pasted.

FIG. 5 shows an example of a deoxidizer package to which the oxygen indicator depicted in FIG. 3 has been pasted. FIG. 6 shows an example of a deoxidizer package to which the oxygen indicator depicted in FIG. 2 has been pasted. With either oxygen indicator, the tape-shaped oxygen indicating agent is bonded to the single-sided self-adhesive plastic tape at the portions C and C' as shown in FIG. 1.

A method and apparatus for obtaining such an oxygen indicator is hereinafter described in detail. This apparatus is an improvement of the apparatus for manufacturing an indicator-equipped small pouch, as described in Japanese Utility Model Registration No. 2,564,282.

Figure 7:
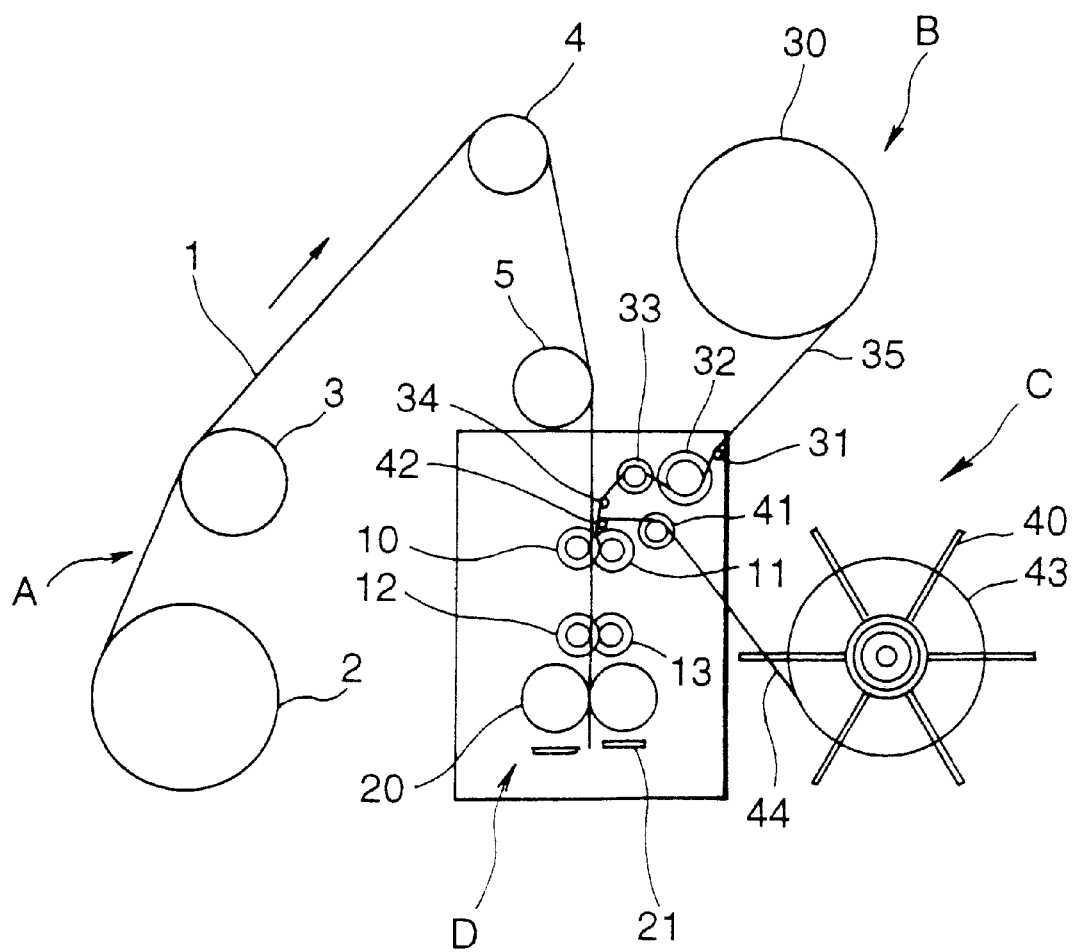
FIG. 7 is a block diagram depicting an example of a manufacturing apparatus for implementing the manufacturing method of this invention.

FIG. 7 is a conceptual diagram depicting an example of the apparatus for manufacturing such indicator-equipped small pouches. The apparatus is composed of: a packaged strip automatic feed unit A for sequentially and automatically feeding a deoxidizer strip 1 as a packaged strip of small pouches, which is composed of a plurality of deoxidizer pouches connected in a strip; an oxygen indicating agent automatic feed unit B for sequentially and continuously feeding out a tape-shaped oxygen indicating agent 35, which is obtained by fixing an oxygen indicator composition to a tape-shape, substrate, toward the deoxidizer strip 1 as an adherend (or object); a self-adhesive tape automatic feed unit C for continuously feeding out the single-sided self-adhesive plastic tape 44 described above toward the deoxidizer strip 1; and unit D for forming separate small pouches equipped with oxygen indicators by pasting and fixing the tape-shaped oxygen indicating agent 35 to the deoxidizer strip 1 and then cutting the packaged small-pouch strip with oxygen indicators so formed into individual small pouches.

The small pouches equipped with the oxygen indicators as discharged from unit D are thrown via a chute to a conveyor line of a packaging machine or the like, are then filled with food in the course of automatic bagging, and are sealed, thereby yielding packaged pouches.

The aforementioned automatic feed unit A comprises a deoxidizer strip uncoiler 2 ,(which carries a given amount of the deoxidizer strip 1 rolled around a drum (cylinder) and guide rollers 3, 4, and 5. The deoxidizer strip 1 is fed out sequentially and automatically from the uncoiler 2 through the guide rollers 3, 4, and 5 to the subsequent steps, first to unit B for automatically feeding the tape-shaped oxygen indicating agent 35, and then to unit C for automatically feeding the single-sided self-adhesive tape 44 to the deoxidizer strip 1.

Unit B comprises a single-sided self-adhesive tape uncoiler 30 for feeding out the oxygen indicating agent 35 through guide rollers 31 through 34 to the deoxidizer strip 1. In addition, the aforementioned unit C comprises: a self-adhesive tape roller 43 for feeding out the single-sided self-adhesive plastic tape 44 through guide rollers 41 and 42 toward the aforementioned deoxidizer strip 1; and a tape uncoiler 40 which carries the roller 43.

The aforementioned unit D comprises: compression bonding means for bonding the single-sided self-adhesive tape 44 to the deoxidizer strip 1 while the aforementioned oxygen indicating agent 35 is interposed between them; and a cutter mechanism that includes a cutter 21 for cutting the deoxidizer strip 1 with oxygen indicators into individual small pouches. As the structure and operation of the cutter mechanism, those described in the aforementioned Japanese Utility Model Registration No. 2,564,282 can be applied.

The aforementioned deoxidizer strip 1 has a structure in which a plurality of small deoxidizer pouches are connected together with the aid of seal portions in the lengthwise direction. This structure is identical to the one described in FIGS. 2 and 3 and in relevant descriptions of the same official gazette of the utility model registration mentioned above.

The compression bonding means is used to form the tape-shaped oxygen indicator as shown in FIG. 1 from the oxygen indicating agent 35 and the single-sided self-adhesive tape 44 and at the same time to paste, bond, or attach such tape-shaped oxygen indicator to the deoxidizer strip 1. As explained in relation to FIG. 1, the tape-shaped oxygen indicating agent 51 is bonded to the approximate center (in the width direction) of the single-sided self-adhesive tape 52, and portions C and C' of the adhesive 54 (where the tape-shaped oxygen indicating agent 51 is not adhesively attached) are formed on both margin sides (in the lengthwise direction) of the single-sided self-adhesive tape 52. In order to obtain such a structure, the oxygen indicating agent 35 and the single-sided self-adhesive tape 44 are sent through the aforementioned feed units to the compression bonding means.

In Embodiment 1, two groups of compression bonding means are provided in the feed direction of the deoxidizer strip 1. Reference numerals 10 and 11 form one group of compression bonding means and reference numerals 12 and 13 form another group of compression bonding means. Reference numerals 10 and 12 denote compression bonding rubber rollers; and reference numerals 11 and 13 denote compression bonding rollers. The deoxidizer strip 1, the oxygen indicating agent 35 and the single-sided self-adhesive tape 44 are caused to pass between these compression bonding rollers and to be compressed and bonded to each other, thereby forming the deoxidizer strip 1 equipped with the tape-shaped oxygen indicator as explained in relation to FIG. 1. Subsequently, the deoxidizer strip 1 is guided into the cutter mechanism 21 by a feed roller 20.

Figure 8:
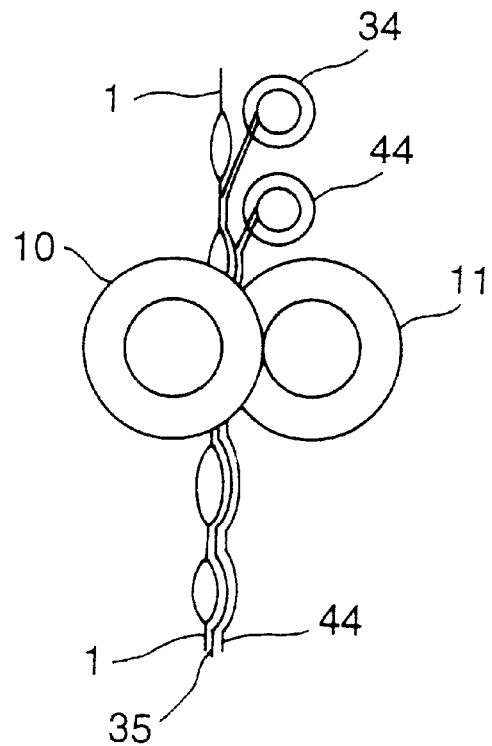
FIG. 8 is an enlarged view of a part of the block diagram shown in FIG. 5.

FIG. 8 is an enlarged view of a part of the aforementioned manufacturing apparatus. FIG. 8 depicts the state in which the single-sided self-adhesive tape 44 is bonded, with the intermediary of the oxygen indicating agent 35, to the deoxidizer strip 1 where small deoxidizer pouches are connected with each other in a continuous arrangement with the aid of seal portions in the lengthwise direction.

Figure 9:
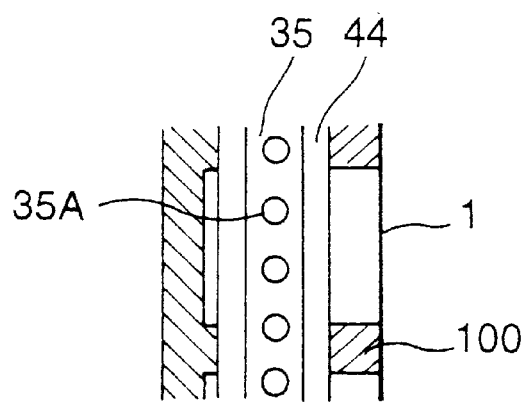
FIG. 9 is a front view of a deoxidizer strip to which the tape-shaped oxygen indicating agent of this invention has been fixed.

FIG. 9 is a front view of the front surface of the deoxidizer strip 1 equipped with the tape-shaped oxygen indicator. The approximate center (in the width direction) of the single-sided self-adhesive tape 44 is aligned with and bonded to the center (in the width direction) of the deoxidizer strip 1 in a manner such that the approximate center (in the width direction) of the oxygen indicating agent 35 substantially coincides with the center (in the width direction) of the deoxidizer strip 1. The aforementioned cutter mechanism 21 cuts the seal portions 100 of the deoxidizer strip 1 with a cutter. Reference numeral 35A indicates a pattern of the oxygen indicator composition fixed to the substrate.

The present invention will be hereinafter described in more details, but the present invention is not limited by such descriptions. The colors of the oxygen indicating agent in Example 1A are indicated with color symbols of color samples (color selector) published by GE Kikaku Center. The color symbols are described in Table 1.

EXAMPLE 1A

Preparation of Oxygen Indicator Composition

Ink containing the following components was prepared: fine magnesium hydroxide powder as an alkaline substance, fructose as a reducing agent, and methylene blue (C. I. Basic Blue 9) as a colorant of which color can be changed by the reducing agent, as well as ethyl cellulose as a binder resin, phloxine (C. I. Acid Red 92) as a colorant of which color cannot be changed by the reducing agent, and water-methanol as a solvent.

Preparation of Tape-Shaped Oxygen Indicating Agent

The following two types of rollers were set in a gravure printing machine in the order indicated as follows: two rollers for diagonal stripe printing with a line width of 5 mm, a line interval of 5 mm, and a print depth of 80 microns; and one roller for solid printing with a print depth of 40 microns. This printing machine was used to print the ink of the above-described oxygen indicator composition by stripe printing and to print an overprint agent (Thermolite P) by solid printing on one side of polypropylene-based synthetic paper (trade name: Yupo, manufactured by Oji Paper; thickness: 70 microns). The moisture content of the printed product was measured to be no more than 0.5% by performing a heating loss method for 70 minutes at a temperature of 105° C., eliminating moisture essentially completely. This printed product was slit into widths of 5 mm, thereby obtaining a tape-shaped oxygen indicating agent in the form of a roll containing 100 m of rolled-up tape. The ink thickness in the printed areas was 20 microns.

Preparation of Single-Sided Self-Adhesive Tape

An acrylic adhesive was applied to the entire surface of a back-printed oriented polypropylene film (thickness: 40 microns) on one side, and a silicone-based release agent was applied to the entire surface of the film on the other side. The obtained product was then slit into widths of 12 mm and was rolled up in a 100 m segment around a 3 inch paper tube, thereby obtaining a single-sided self-adhesive tape which has a continuous transparent portion with a width of 4 mm extending in the lengthwise direction in the approximate center (in the width direction), and in which white characters were printed on a greenish-gray background in the remaining areas.

Preparation of Tape-shaped Oxygen Indicator

The aforementioned tape-shaped oxygen indicating agent and the aforementioned single-sided self-adhesive tape were

TABLE 1(*1)

| | Color Expression (CS Number) | | | | | | | |
|---|---|---|---|---|---|---|---|---|
| | Color | | | | | | | |
| Blue/Red Ratio | Indigo 5/3 | 5/4 | 1/1 | Purple 4/5 | 3/5 | Red 2/5 | 1/5 | 0/1 |
| Color Depth | | | | | | | | |
| Very Pale | CS20-02 | CS21-02 | CS22-02 | CS23-02 | CS24-02 | CS25-02 | CS26-02 | CS27-02 |
| Pale | CS20-03 | CS21-03 | CS22-03 | CS23-03 | CS24-03 | CS25-03 | CS26-03 | CS27-03 |
| Standard | CS20-04 | CS21-04 | CS22-04 | CS23-04 | CS24-04 | CS25-04 | CS26-04 | CS27-04 | respectively fed to an apparatus comprising two vertically arranged groups of unwinding rollers, guides, and winding rollers; the tape-shaped oxygen indicating agent and the single-sided self-adhesive tape and, while being unwound, were aligned in a manner such that the tape-shaped oxygen indicating agent was located in the approximate center (in the width direction) of the single-sided self-adhesive tape, and that the oxygen indicator composition and the self-adhesive surface were brought into contact with each other and were placed one over the other; and a 100 m segment of the obtained product was rolled around a 3 inch paper tube on the winding roller, thereby obtaining a tape-shaped oxygen indicator having the structure as shown in FIG. 3. This oxygen indicator changed its color to CS21-04 (dark blue) in air, and to CS26-04 (red) in an atmosphere in which the oxygen concentration had been brought down to no more than 0.1% by using a deoxidizer.

Preparation and Storage of Deoxidizer Package with Oxygen Indicator Pasted Thereon A pasting apparatus comprising unwinding rollers, guides, compression bonding rollers, a thickness gauging roller, and a cutter was used to unwind and guide a roll of packaged deoxidizer strip (trade name: Ageless SA-100R, manufactured by Mitsubishi Gas Chemical Co., Inc.), and the aforementioned tape-shaped oxygen indicator was placed over and pasted on one side of the packaged deoxidizer strip with the aid of the compression bonding rollers. The resultant deoxidizer package was cut into individual pieces with the cutter that is operated in conjunction with the thickness gauge roller, thereby yielding deoxidizer packages equipped with oxygen indicators pasted thereon. Groups of such indicators (100 each) were put into flat bags (220 mm×300 mm) made of a laminated gas-permeation-resistant film (KON/PE), the air inside the bags was removed, and the mouths of the bags were heat-sealed. The resulting bags were stored in an air-conditioned storage room at a temperature of 15° C.

Measurement 1. Color Change Rate of Oxygen Indicator

A deoxidizer package with an oxygen indicator pasted thereon was put in a gas-permeation-resistant bag (180 mm×250 mm) together with 500 ml of air and absorbent cotton impregnated with a humidifying solution (80% RH), and the bag was then hermetically sealed. Small amounts of the gas inside the bag were sampled with the passage of time. Concerning the deoxidizer package with the oxygen indicator pasted thereon before storage and after one month storage, the oxygen concentration was measured using an oxygen analyzer manufactured by Toray, and changes in the color of the oxygen indicator were monitored. The results are shown in Table 2.

Measurement 2. Tests Involving Actual Food

The deoxidizer package provided with the oxygen indicator pasted thereon prior to storage was put in a gas-permeation-resistant bag (180 mm×250 mm) together with two doughnuts, and the bag was then hermetically sealed and was stored indoors at a temperature of 25° C. Changes in the color of the oxygen indicator were monitored with the passage of time, the bag was opened after one month storage, and changes in the color of the oxygen indicator were observed. The results are shown in Table 3.

EXAMPLE 1B

A deoxidizer package equipped with an oxygen indicator pasted thereon was prepared in the same manner as in Example 1A, except that an oriented polyester film (thickness: 40 microns) was used for the single-sided self-adhesive tape instead of oriented polypropylene to fabricate the tape-shaped oxygen indicating agent. Measurements 1 and 2 were conducted with this deoxidizer package in the same manner as in Example 1A. The results are as indicated in Table 2 and 3.

EXAMPLE 1C

A deoxidizer package equipped with an oxygen indicator pasted thereon was prepared in the same manner as in Example 1A, except that a synthetic rubber adhesive was used for the adhesive of the single-sided self-adhesive tape instead of the acrylic adhesive to fabricate the tape-shaped oxygen indicating agent. Measurements 1 and 2 were conducted with this deoxidizer package in the same manner as in Example 1A. The results are as indicated in Table 2 and 3.

COMPARISON 1

The tape-shaped oxygen indicating agent prepared in Example 1A and a double-sided adhesive tape with a width of 5 mm were fed into the pasting apparatus used in Example 1A. The unprinted side of the tape-shaped oxygen indicating agent and one side of a packaged deoxidizer strip in a roll were pasted together with the aid of the double-sided adhesive tape, and the deoxidizer package was cut into individual packages with the aid of the cutter operating in conjunction with the thickness gauge roller, thereby yielding a deoxidizer package to which the tape-shaped oxygen indicating agent was fixed with the double-sided adhesive tape. This obtained product was used to perform Measurements 1 and 2 in the same manner as in Example 1. The results are ,shown in Tables 2 and 3.

COMPARISON 2

A tape-shaped oxygen indicating agent was prepared in the same manner as in Example 1, except that water- and oil-resistant paper (trade name: WOP, manufactured by Chuetsu Pulp; thickness: 80 microns) was used instead of the polypropylene-based synthetic paper. Except for the use of this tape-shaped oxygen indicating agent, a deoxidizer package to which the oxygen indicator tape was fixed with a double-sided adhesive tape was then prepared in the same manner as in Comparison 1. This deoxidizer package was used to perform, Measurements 1 and 2. The results are shown in Tables2 and 3.

TABLE 2

Color Change Rates of Oxygen Indicators

| | Example 1A | Example 1B | Example 1C | Comparison 1 | Comparison 2 |
|---|---|---|---|---|---|
| Before storage | | | | | |
| Color of oxygen indicator prior to measurement | CS21-04 | CS21-04 | CS21-04 | CS21-04 | CS21-04 |
| Time needed for oxygen concentration inside bag to reach 0.1% | 12 hours | 12 hours | 12 hours | 12 hours | 12 hours |

TABLE 2-continued

Color Change Rates of Oxygen Indicators

|  | Example 1A | Example 1B | Example 1C | Comparison 1 | Comparison 2 |
|---|---|---|---|---|---|
| Time needed for oxygen indicator to acquire color CS-26 | 12 hours | 11 hours | 12 hours | 15 hours | 17 hours |
| Color displayed upon reaching CS-26 After 1-month storage | CS26-04 | CS26-04 | CS26-04 | CS26-04 | CS26-04 |
| Color of oxygen indicator prior to measurement | CS21-04 | CS21-04 | CS21-04 | CS21-02 | CS21-02 |
| Time needed for oxygen concentration inside bag to reach 0.1% | 12 hours | 12 hours | 12 hours | 12 hours | 12 hours |
| Time needed for oxygen indicator to acquire color CS-26 | 12 hours | 15 hours | 12 hours | 17 hours | 20 hours |
| Color displayed upon reaching CS-26 | CS26-04 | CS26-04 | CS26-04 | CS26-02 | CS26-02 |

TABLE 3

Results of Tests Involving Actual Food

|  | Example 1A | Example 1B | Example 1C | Comparison 1 | Comparison 2 |
|---|---|---|---|---|---|
| Oxygen Indicator Color over days |  |  |  |  |  |
| After 10 days | ○ | ○ | ○ | ○ | Δ |
| After 20 days | ○ | ○ | ○ | ○ | x |
| After 30 days | ○ | ○ | ○ | Δ | x |
| Color of Oxygen Indicator When the Bag Was Opened after 30 Days Storage | CS21-04 | CS21-04 | CS21-04 | CS23-02 | No change in color |

○ The color CS26-04 was maintained.
Δ Blurring of the color or partial color changes were observed.
x Large blurring of the color was observed and it was difficult to distinguish the color.

The results of Measurement 1 (Table 2) show that the oxygen indicator of Example 1A rapidly assumed the color CS26 promptly after the oxygen concentration inside the bag (either before or after storage) reached 0.1%, and that there was no paling of the color. This indicates that the oxygen indicator of the present invention has an excellent oxygen concentration indicating function and also an excellent storage stability. On the contrary, the oxygen indicators of Comparisons 1 and 2 exhibited delayed color changes even before storage. After these indicators were stored for some time, their color changing rate decreased dramatically, and, their color became pale and difficult to distinguish. This is assumably because subtle changes in the oxygen indicator composition were induced by the humidity (97%RH, 25° C.) of the deoxidizer package. Specifically, the deoxidizer package obtained by using the limitedly moisture-permeable tape-shaped oxygen indicating agent exhibited better performance than those using the moisture-permeable oxygen indicating agent. Accordingly, it is assumed that the transition of colorants in the thickness direction due to moisture permeation is one of the factors that cause changes in performance.

Moreover, the results of Measurement 2 (Table 3) indicate that in Comparisons where the single-sided self-adhesive tape was not used, the oxygen indicators assumed abnormal colors duel to the influence of oil and moisture from the doughnuts, and could not return to the blue color when the bags were opened and the oxygen indicators were exposed to the air, and the color of the oxygen indicators were pale. On the other hand, the results of the measurement shows that the oxygen indicator of Example 1A maintained the color adequately and also maintained the color changing performance even after the bag was opened.

EXAMPLE 2

The oxygen indicator roll of Example 1A was put in an office tape dispenser (trade name: T-M12; manufactured by Kokuyo). The oxygen indicator was pulled out in appropriate lengths by hand and was then cut in the same manner as in the case of a self-adhesive tape for office use, and such pulling and cutting actions were repeated. In this way, the oxygen indicator roll was easily cut into pieces of any length without any problem. The oxygen indicator (cut into a length of 1 cm) was pasted to the back side of a polystyrene plate (150 cm×110 cm), a deoxidizer package (trade name: Ageless FX-30, manufactured by Mitsubishi Gas Chemical) and 70 g of a dried fish/cheese snack were placed together on the plate, and they were put in a gas-permeation-resistant bag (150 mm×200 mm), and the mouth of the bag was heat-sealed. At that time, the color of the oxygen indicating agent was CS21-04. When the bag was stored in a 5° C. thermostat, the oxygen concentration in the bag decreased to 0.02% the next day, and the color of the oxygen indicating agent changed to CS26-04. A pinhole was then made in the bag with a sewing needle, and the oxygen concentration in the bag was measured the next day and was found to have increased to 0.4%. At that time, the color of the oxygen indicating agent changed to CS24-04, and it was possible to tell the abnormal condition in the bag. After two more days, the oxygen concentration in the bag had increased to 12%, and the color of the oxygen indicator changed to CS22-04. To measure the oxygen concentration in the bag, small amounts of the gas from the bag were sampled and analyzed using gas chromatograph. It was found that the oxygen indicator of the present invention accurately reflects the condition in a packaging container and change its color when any accident happens in a food packaging container equipped with a deoxidizer and when the atmosphere in the packaging container is no longer in the deoxidized state.

The oxygen indicator of the present invention has a simple structure and can, therefore, be manufactured at low cost. Moreover, since the oxygen indicator can be made in a thin tape shape just like a common single-sided self-adhesive tape, it can be used after being cut into any lengths with a simple tool. Furthermore, the oxygen indicator can be automatically manufactured, cut, and pasted using mechanical means, and is very easy to use. The oxygen indicator changes its color very rapidly in response to changes in oxygen concentration, thereby facilitating visual observation of the oxygen concentration.

The oxygen indicator does not exhibit abnormal colors in highly moist or oily environment, can be safely used for the quality control of packaged foods provided with deoxidizers, does not deteriorate in terms of color or color change rate when stored after being pasted on deoxidizer packages or inside packaging containers, and exhibits excellent performance as an oxygen indicator. The ability of the oxygen indicator to indicate oxygen concentration with the color and to maintain an excellent color change rate and color stability can also be used in applications other than packaging in the deoxidized state, such as in applications involving the packaging of foods and other various products, and in applications for the safety management of various types,of equipment. In these applications, the oxygen indicator can be used as easily and handily as commercially available self-adhesive tapes, labels, or stickers.

This invention achieves such advantageous effect that the oxygen indicator can change its color rapidly in response to a reduction in the oxygen concentration of a packaging container or bag as induced by a deoxidizer, thereby making it easier to detect the reduction of the oxygen concentration visually and without a time lag.

EMBODIMENT 2

Figure 10:
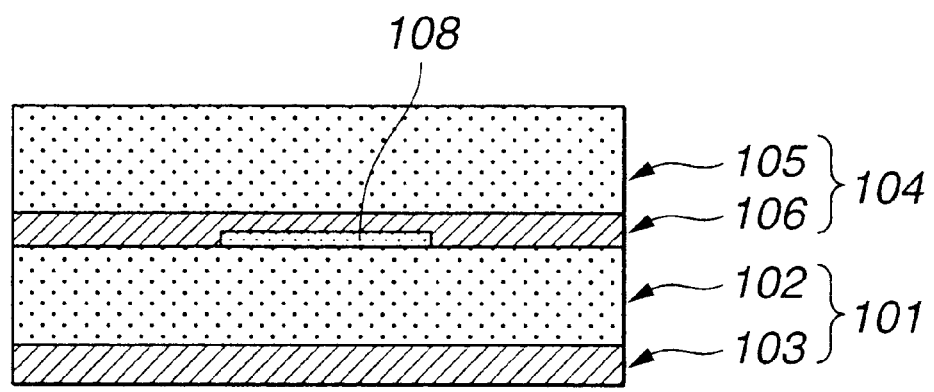
FIG. 10 is a cross-sectional view of a preferred oxygen indicator according to Embodiment 2.
Figure 11:
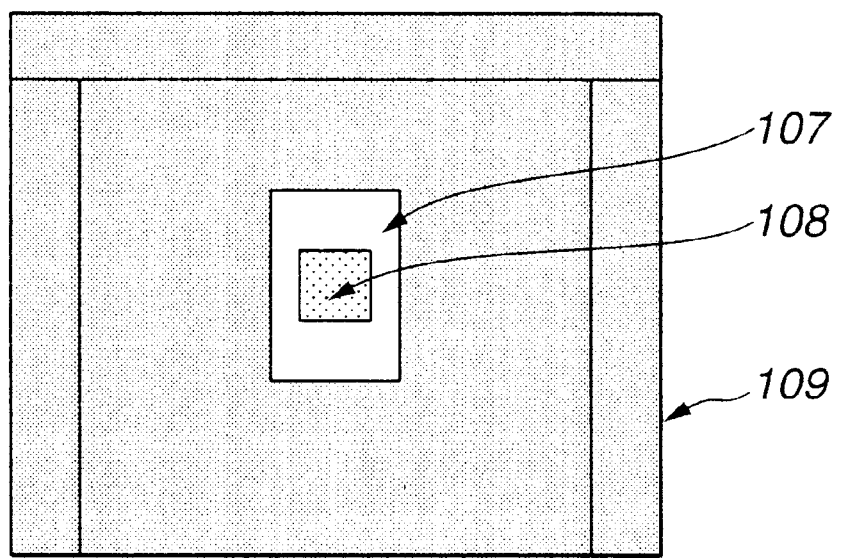
FIG. 11 is a diagram depicting an example of a deoxidizer package to which the oxygen indicator according to Embodiment 2 has been pasted.
Figure 12:
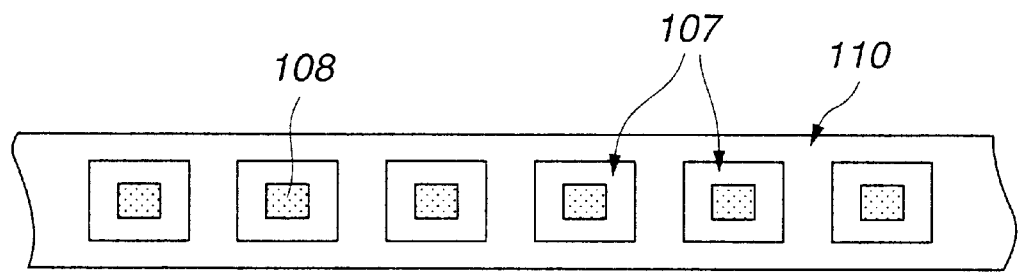
FIG. 12 is a diagram depicting a preferred example of an adhesive oxygen indicator web where label-shaped oxygen indicators according to Embodiment 2 are placed over release paper at regular intervals.

FIG. 10 is a cross-sectional view of a preferred oxygen indicator according to Embodiment 2. This oxygen indicator is characterized in that a single-sided self-adhesive tape 104 is provided on an oxygen indicator composition attached surface of a label-shaped oxygen indicating agent 101. The label-shaped oxygen indicating agent 101 is composed of a label substrate 102 and a label self-adhesive layer 103. The single-sided self-adhesive tape 104 is composed of a tape substrate 105 and a tape self-adhesive layer 106. The oxygen indicator composition 108 is applied or printed over a part of or the entire surface of the label substrate 102. FIG. 11 is a diagram depicting an example of a deoxidizer package to which the oxygen indicator according to Embodiment 2 has been attached. FIG. 12 is a diagram depicting a preferred example of an adhesive oxygen indicator web where label-shaped oxygen indicators according to Embodiment 2 are placed over release paper at regular intervals.

Embodiment 2 is hereinafter explained in more detail with reference to examples.

EXAMPLE 3

Preparation of Oxygen Indicator Composition

The oxygen indicator composition was prepared in the same manner as in Embodiment 1.

Preparation of Label-Shaped Oxygen Indicator

The ink used in the preparation of the oxygen indicator composition was applied by means of gravure and dried in the shape of squares (each with length 4 mm×width 4 mm) at plural positions at regular intervals over the surface of polyethylene-based synthetic paper (trade name: Yupo, manufactured by Oji Paper; thickness: 70 microns). Subsequently, a synthetic rubber elastomer adhesive was applied over the surface of the synthetic paper where the ink was not applied, thereby forming an self-adhesive layer, to which release paper was then attached. To the surface of the synthetic paper where the ink was applied, a transparent single-sided self-adhesive tape (trade name: PL SHIN/7HL, manufactured by: Lintech K. K.) which was made of an oriented polypropylene film, which was coated with an acrylic adhesive on the entire surface of one side thereof, and which was 20 $\mu$m thick was attached. Then, a cutting die was used to conduct half, die cutting of the laminated layers obtained above in the shape of a quadrangle (length 10 mm×width 16 mm) by setting the center of the quadrangle at the position where the ink had been applied, and by leaving the release paper uncut, thereby obtaining a label-shaped oxygen indicator of which peripheral portions had been removed by half die cutting and which was being pasted to the release paper. At the end, the release paper was cut and rolled around a paper tube, thereby obtaining an oxygen indicator web where oxygen indicators are arranged in a line at regular intervals over the release paper.

Color Changing Performance of the Label-Shaped Oxygen Indicator

One of the oxygen indicators obtained above was peeled from the release paper and was pasted to a deoxidizer package (trade name: Ageless SA-100, manufactured by Mitsubishi Gas Chemical). The deoxidizer package with the oxygen indicator pasted thereon was put in a gas-permeation-resistant bag together with 500 ml of air and absorbent cotton impregnated with a humidifying solution to make the atmosphere humidity 80% RH, and the bag was then hermetically sealed and was preserved indoors at a temperature of 25° C. Small portions of the gas inside the bag were sampled every specified period of time, the oxygen concentration was measured using a zirconia oxygen analyzer, and changes in the color of the oxygen indicating agent were monitored. The results are shown in Table 4. The oxygen concentration within the bag reached 0.1% after 12 hours, and the pasted oxygen indicating agent became pink at the same time as the oxygen concentration within the bag reached 0.1%. This oxygen indicating agent turned blue in the open air.

EXAMPLE 4

A label-shaped oxygen indicator was prepared in the same manner as in Example 3, except that as the single-sided self-adhesive tape to be pasted to the surface where the oxygen indicating agent was printed, a transparent single-sided self-adhesive tape (trade name: PL SHIN/7LK, manufactured by Lintech K. K.) was used, which was made of polyethylene terephthalate, which was coated with an acrylic adhesive on the entire surface on one side thereof, and which was 16 $\mu$m thick, instead of the oriented polypropylene film self-adhesive tape. The results of evaluation of the color changing performance of this label-shaped oxygen indicator are shown in Table 4. The oxygen concentration within the bag reached 0.1% after 12 hours, and the pasted oxygen indicating agent became pink at the same time as the oxygen concentration within the bag reached 0.1%. This oxygen indicating agent turned blue in the open air.

EXAMPLE 5

A label-shaped oxygen indicator was prepared in the same manner as in Example 3, except that the oxygen indicator was put in the bag together with absorbent cotton impregnated with water to make the humidity 100%, instead of the absorbent cotton impregnated with the humidifying agent to make the humidity 80% in the gas-permeation-resistant bag. The results of evaluation of the preservation performance of this label-shaped oxygen indicator are shown in Table 5. The oxygen concentration within the bag reached 0.1% after 12 hours, and the pasted oxygen indicator became pink at the same time as the oxygen concentration within the bag reached 0.1% and maintained the pink color even after 90 days.

EXAMPLE 6

A very high speed automatic label pasting machine (trade name: improved AL model, manufactured by K. K. Satoh)

was loaded with the web as obtained in Example 3, where the label-shaped oxygen indicators were arranged in line at regular intervals over the release paper. In combination with an automatic filling and packaging machine for the production of deoxidizers, tit was possible to produce deoxidizers with the label-shaped oxygen indicators pasted thereon in the amount of 500 units per minute at high speed without a hitch.

COMPARISON 3

A label-shaped oxygen indicator was prepared in the same manner as in Example 3, except that a single-sided self-adhesive tape was not pasted to the side where an oxygen indicating agent was printed. The results of evaluation of the color changing performance of the label-shaped oxygen indicator are shown in Table. 4. The oxygen concentration within the bag reached 0.1% after 12 hours. While the label-shaped oxygen indicating agent was blue in the air, it turned purple, the color at an intermediate stage in the color changing process, when the oxygen concentration within the bag reached 0.1%. One day later, the oxygen indicating agent turned pink. This means that the label-shaped oxygen indicating agent changed its color behind a time lag in response to the decrease in the oxygen concentration in the bag.

COMPARISON 4

A label-shaped oxygen indicator was prepared in the same manner as in Example 3, except that instead of the oriented polypropylene film self-adhesive tape serving as the single-sided self-adhesive tape pasted to the side where the oxygen indicating agent was printed, gas- and moisture-permeable woodfree, paper was used, and that the single-sided self-adhesive tape was not pasted to the side where the oxygen indicating agent was printed. The results of evaluation of the color changing performance of the label-shaped oxygen indicator are shown in Table. 4. The oxygen concentration within the bag reached 0.1% after 12 hours. The label-shaped oxygen indicating agent which had been blue in the air was then still blue. One day later, the oxygen indicator turned pink. This means that the label-shaped oxygen indicator changed its color behind a time lag in response to the decrease in the oxygen concentration in the bag.

COMPARISON 5

The preservation performance was evaluated in the same manner as in Comparison 3, except that the oxygen indicator was put in the bag in a hermetically sealed manner together with absorbent cotton impregnated with a humidifying agent to make the humidity 100% in a gas-permeation-resistant bag, instead of the absorbent cotton impregnated with the humidifying agent to make the humidity 80% within the bag. The results are shown in Table 5. This label-shaped oxygen indicator maintained the pink color after 30 days, but turned purple after 60 days.

COMPARISON 6

The preservation performance was evaluated in the same manner as in Comparison 4, except that the oxygen indicator was put in the bag in a hermetically sealed manner together with absorbent cotton impregnated with a humidifying agent to make the humidity 100% in a gas-permeation-resistant bag, instead of the absorbent cotton impregnated with the humidifying agent to make the humidity 80% within the bag. The results are shown in Table 5. This label-shaped oxygen indicator maintained the pink color after 10 days, but turned purple after 15 days and then turned blue after 30 days.

TABLE 4

Color Changing Performance of Label-Shaped Oxygen Indicating Agent (25° C., 80% RH)

|  | Example 3 | Example 4 | Comp. 3 | Comp. 4 |
| --- | --- | --- | --- | --- |
| Color of the Oxygen Indicating Agent at the Beginning of Measurement | Blue CS2204-2304 | Blue CS2204-2304 | Blue CS2204-2304 | Blue CS2204-2304 |
| Color of the Oxygen Indicating Agent When Oxygen Concentration within the Bag Reached 0.1% | Pink CS2604-2704 | Pink CS2604-2704 | Purple CS2404-2504 | Blue CS2204-2304 |
| Color of the Oxygen Indicating Agent after One Day | Pink CS2604-2704 | Pink CS2604-2704 | Pink CS2604-2704 | Pink CS2604-2704 |

TABLE 5

Preservation Performance of Label-Shaped Oxygen Indicating Agent (25° C., 100% RH)

|  | Example 5 | Comparison 5 | Comparison 6 |
| --- | --- | --- | --- |
| Color of the Oxygen Indicating Agent after 1 Day | Pink CS2604-2704 | Pink CS2604-2704 | Pink CS2604-2704 |
| Color of the Oxygen Indicating Agent after 10 Days | Pink CS2604-2704 | Pink CS2604-2704 | Pink CS2604-2704 |
| Color of the Oxygen Indicating Agent after 15 Days | Pink CS2604-2704 | Pink CS2604-2704 | Purple CS2404-2504 |
| Color of the Oxygen Indicating Agent after 30 Days | Pink CS2604-2704 | Pink CS2604-2704 | Blue CS2204-2304 |
| Color of the Oxygen Indicating Agent after 60 Days | Pink CS2604-2704 | Purple CS2404-2504 | Blue CS2204-2304 |
| Color of the Oxygen Indicating Agent after 90 Days | Pink CS2604-2704 | Purple CS2404-2504 | Blue CS2204-2304 |

Concerning the oxygen indicator according to Embodiment 2, the side of the, oxygen indicator to which the oxygen indicating composition is attached is covered with the transparent single-sided self-adhesive tape which is limitedly permeable to gas and moisture, and the oxygen indicator is in a label shape which has the self-adhesive surface on its back side. Accordingly, the oxygen indicator according to Embodiment 2 is resistant to water and oil and the manufacturing cost is reduced. Moreover, when integrated with the deoxidizer package, the oxygen indication will neither cause any sense of a cumbersome existence nor give any impact on the capabilities of the deoxidizer. Consequently, the oxygen indicator according to Embodiment 2 can be applied with extreme availability to the field of maintaining quality of food and the like by using deoxidizers.

Furthermore, the web where a plurality of the oxygen indicators according to Embodiment 2 are pasted via their self-adhesive surfaces on their back sides to the release paper can be pasted to the deoxidizer package or the like readily after it is peeled off from the release paper. Accordingly, the manufacturing cost is reduced and it becomes possible to perform high-speed pasting with the automatic pasting machine, thereby improving the productivity.

EMBODIMENT 3

Figure 13:
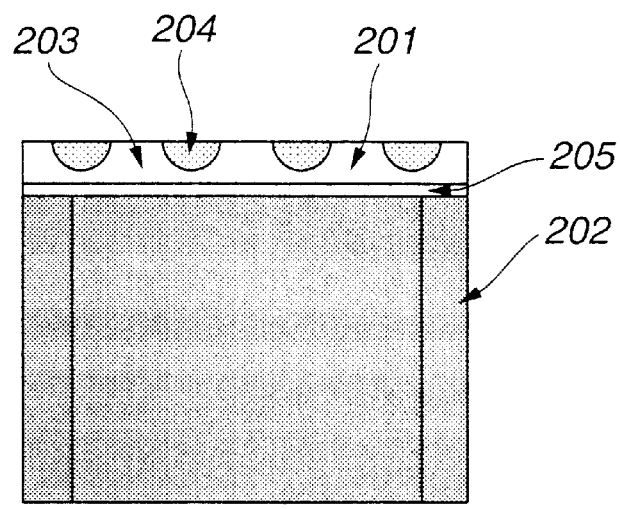
FIG. 13 is a diagram depicting a preferred example of a deoxidizer package with an oxygen indicating function according to Embodiment 3.

A preferred mode according to Embodiment 3 is a deoxidizer package with an oxygen indicating function, to which a tape-shaped oxygen indicator having an oxygen indicator composition is pasted with a transparent and limitedly gas- and moisture-permeable single-sided self-adhesive tape in a manner that the oxygen indicator and the tape enclose the peripheral seal portion of the deoxidizer package. FIG. 13 is a diagram depicting an example of such deoxidizer package. An explanation is hereinafter given with reference to FIG. 13.

Concerning the deoxidizer package with the oxygen indicating function of this invention, a tape-shaped oxygen indicator 201 is pasted to the peripheral seal portion of a deoxidizer package 202 to which three-side sealing has been applied. As air holes of the deoxidizer package 202 are not blocked, the oxygen absorbing capability of the deoxidizer does not degrade. Moreover, since the peripheral seal portion is extremely thin as compared with the center or deoxidizer-filled portion of the deoxidizer package 202, even if it is used for the preservation of food or the like containing much oil, such a phenomenon will not occur that the oxygen indicating agent may closely contact the packagingbag, and the deoxidized state of the atmosphere will be properly reflected. Moreover, since the oxygen indicator is pasted to the deoxidizer package 202 in a manner such that the oxygen indicator is held within the peripheral seal portion of the deoxidizer package 202, color changes of the oxygen indicating agent 204 are visible from either side of the deoxidizer package 202.

Concerning the tape-shaped oxygen indicator 201 so pasted, an oxygen indicator composition 204 printed on a substrate 203 is coated with a single-sided self-adhesive tape 205 which is limitedly permeable to gas and moisture and is transparent. Accordingly, the tape-shaped oxygen indicator 201 is resistant to water and oil. Therefore, such problems will not occur, that moisture or oil may penetrate into the oxygen indicator composition 204 and impair the color changing function.

A deoxidizer package with an oxygen indicating function can also be used, to which a tape-shaped oxygen indicator having an oxygen indicator composition is pasted with a self-adhesive layer provided on the back side of the substrate in a manner that the oxygen indicator encloses the peripheral seal portion of the deoxidizer package.

Embodiment 3 is hereinafter explained in more detail with reference to examples.

EXAMPLE 7

Preparation of Oxygen Indicator Composition

The oxygen indicator composition was prepared in the same manner as in Embodiment 1.

Preparation of Tape-Shaped Oxygen Indicator

The aforementioned ink was applied by means of gravure and dried in the shape of circles, each with a diameter of 5 mm, over the surface of polyethylene-based synthetic paper (trade name: Yupo, manufactured by Oji Paper; thickness: 70 microns). Subsequently, the obtained printed product was cut along each line of the circles into strips of the width of 15 mm and was rolled around a paper tube, thereby obtaining a web where a plurality of tape-shaped oxygen indicators are connected in line.

Preparation of Deoxidizer Package with Oxygen Indicating Function

The tape-shaped oxygen-indicator was covered with a single-sided self-adhesive tape (trade name: Cutron Tape No. 810, manufactured by Sekisui Chemical, Co., Ltd.) (width: 25 mm; thickness: 40 $\mu$m) of which width is wider than the tape-shaped oxygen indicator, which has a substrate made of an oriented polypropylene film, and which is coated with an acrylic adhesive on the entire surface of one side thereof. The covered oxygen indicator was then folded along the lengthwise direction with the oxygen indicator side facing inward and was pasted to a moisture-dependent deoxidizer(trade name: Ageless FY-100, manufactured by Mitsubishi Gas Chemical Co., Inc.) which is capable of absorbing oxygen from both its surfaces, in a manner such that the oxygen indicator was held within the heat-seal portion at one edge of the deoxidizer, thereby producing the deoxidizer package with an oxygen indicating function.

Performance of Deoxidizer Package with Oxygen Indicating Function

The above-obtained deoxidizer package with the oxygen indicating function was put in a gas-permeation-resistant bag together with 500 ml of air and absorbent cotton impregnated with a humidifying agent to make the humidity 90% RH, and the bag was then hermetically sealed and was preserved indoors at a temperature of 25° C. Small portions of the gas inside the bag were sampled every specified period of time, the oxygen concentration was measured using a zirconia oxygen analyzer, and changes in the color of the oxygen indicating agent were monitored. The oxygen concentration within the bag reached 0.1% after 16 hours. When the oxygen indicator was put in the bag together with air in a hermetically sealed manner, the color of the oxygen indicating agent was blue, which indicates the existence of oxygen. Subsequently, the oxygen indicating agent turned pink within 4 hours after the oxygen concentration within the bag reached 0.1%, and the color and appearance did not change during the 60 day preservation period.

EXAMPLE 8

For the performance evaluation of the deoxidizer package with the oxygen indicating function of Example 7, water was used to make the humidity 100%RH instead of the humidifying agent to make the humidity 90%RH, and the oxygen concentration was measured and the color and appearance of the oxygen indicator were monitored. The oxygen concentration within the bag reached 0.1% after 12 hours. When the oxygen indicator was put in the bag together with air in a hermetically sealed manner, the color of the oxygen indicating agent was blue, which indicates the existence of oxygen. Subsequently, the oxygen indicating agent turned pink within 4 hours after the oxygen concentration within the bag reached 0.1%, and the color and appearance did not change during the 60 day preservation period.

EXAMPLE 9

A deoxidizer package with the oxygen indicating function, in which a tape-shaped oxygen indicator was pasted to the peripheral seal portion of the deoxidizer package, was prepared in the same manner as in Example 7, except that as the deoxidizer package, a self-reactive type deoxidizer (trade name: Ageless SA-30, manufactured by Mitsubishi Gas Chemical, Co., Inc.) was used, which is capable of absorbing oxygen from both surfaces thereof and of which three sides were sealed. The deoxidizer package was put in a gas-permeation-resistant bag together with a piece of wet cake (trade name: "Brownie", made by K. K. Andersen) containing much oil and 150 ml of air, and the bag was then hermetically sealed and was preserved indoors at a temperature of 25° C.

When the oxygen indicator was put in the bag together with air in a hermetically sealed manner, the color of the oxygen indicating agent was blue, which indicates the existence of oxygen. Subsequently, the oxygen indicating agent turned pink almost at the same time as the oxygen concentration within the bag reached 0.1%. The color and appearance did not change during the 30 day preservation period.

EXAMPLE 10

A deoxidizer package with the oxygen indicating function was prepared and its performance was evaluated in the same manner as in Example 7, except that the tape-shaped oxygen indicator was pasted to the center of one surface of the deoxidizer package, but not to the peripheral seal portion of the deoxidizer package. The oxygen concentration within the bag reached 0.1% after 19 hours. This means that the time required for the oxygen concentration to reach 0.1% was extended for 3 hours. When the oxygen indicator was put in the bag together with air in a hermetically sealed manner, the color of the oxygen indicating agent was blue, which indicates the existence of oxygen. Subsequently, the oxygen indicating agent turned pink within 4 hours after the oxygen concentration within the bag reached 0.1%. The color and appearance did not change during the 30 day preservation period.

COMPARISON 7

A deoxidizer package with the oxygen indicating function was prepared in the same manner as in Example 7, except that instead of the tape-shaped oxygen indicator, cotton embroidery threads No. 5 impregnated with oxygen indicating agent components were pasted along the peripheral seal portion of the deoxidizer package. The performance evaluation was conducted in the same manner as in Example 8. It took 14 hours for the oxygen concentration within the bag to reach 0.1%.

When the oxygen indicator was put in the bag together with air in a hermetically sealed manner, the color of the oxygen indicating agent was blue, which indicates the existence of oxygen. Subsequently, the oxygen indicating agent turned pink within 4 hours after the oxygen concentration within the bag reached 0.1%. The oxygen indicating agent then turned reddish pink after 20 days and further turned wet reddish pink after 40 days. It was then confirmed that the oxygen indicating agent components had leaked out from the ends of the threads.

According to Embodiment 3, as compared with the case where the tape-shaped oxygen indicator is pasted to the center of the deoxidizer package, the deoxidizer package with the oxygen indicating function, in which the tape-shaped oxygen indicator is pasted to the peripheral seal portion of the deoxidizer package, exhibits faster oxygen absorbing rate and does not inhibit the oxygen absorbing capabilities that the deoxidizer originally has. When the deoxidizer package is used for the preservation of food or the like containing much oil, the oxygen indicator never comes in close contact with the packaging bag. Therefore, if the food or the like is preserved in the deoxidized atmosphere, the oxygen indicator will never fail to indicate that the atmosphere is in the deoxidized state. There is also such an advantage that the color changes of the oxygen indicator are visible from either side of the deoxidizer package. Moreover, the oxygen indicator composition is covered with the single-sided self-adhesive tape which is limitedly permeable to gas and moisture and is transparent.

As a result, the deoxidizer package is resistant to water and oil and there is no possibility that any contaminants derived from the oxygen indicator may attach to the food or the like. Accordingly, this deoxidizer package is very useful in the field of maintaining the quality of foods, pharmaceuticals and the like.

Since the tape-shaped oxygen indicator according to Embodiment 3 does not become thick, it will not cause a sense of a cumbersome existence. Moreover, since such oxygen indicator can be made in a chip-like label shape, it will not damage the capabilities of a deoxidizer and will not cause a sense of cumbersome existence even when integrated with the deoxidizer. In addition, since the tape-shaped oxygen indicator is pasted to the deoxidizer package in a manner such that the oxygen indicator is held within the peripheral seal portion of the deoxidizer package, it will not damage the deoxidizing capabilities of the deoxidizer package. Furthermore, since the oxygen indicator is covered with the single-sided self-adhesive tape which is limitedly permeable to gas and moisture and is transparent, it is resistant to water and oil.

Specifically concerning the deoxidizer package of the both-side absorbing type, of which both surfaces are made of gas-permeable packaging materials, and to which the tape-shaped oxygen indicator is pasted in a manner such that the oxygen indicator is held within the peripheral seal portion of the deoxidizer package, the oxygen indicating agent will never be hidden regardless of the facing of the deoxidizer package. Accordingly, it has such an advantage when applied to preserved products that the deoxidizer package can be placed with either side facing outside.

What is claimed is:

1. An oxygen indicator comprising:
    an oxygen indicating member including a substrate and an oxygen indicator composition, said substrate having an oxygen permeability of 50–3000 cc/m$^2$ ·day·atm and a moisture permeability of 50 g/ m$^2$·day or lower and said oxygen indicator composition fixed at a first surface of said tie substrate; and
    a single-sided self-adhesive plastic member having a self-adhesive layer on one side thereof,
    wherein said oxygen indicating composition of said oxygen indicating member is adhered to said single-sided self-adhesive plastic member, which consists of polypropylene or polyester and has the oxygen permeability of 50–3000 cc/m$^2$ ·day atm and moisture permeability of 50 g/m$^2$·day or lower and is at least partly transparent, by the self-adhesive layer.

2. The oxygen indicator according to claim 1, wherein said the oxygen indicator composition is fixed at the surface of said the substrate by means of application, printing or impregnation.

3. The oxygen indicator according to claim 1, wherein the width of said single-sided self-adhesive plastic member is wider than that of said oxygen indicating member and said oxygen indicating member is provided at an approximate center position in the width direction of said single-sided self-adhesive plastic member.

4. A deoxidizer package with an oxygen indicating function, wherein the oxygen indicator as stated in claim 1 is provided on the deoxidizer package containing a deoxidizer in a packaging material.

5. A packaging container equipped with an oxygen indicator, wherein the oxygen indicator as stated in claim 1 is pasted to the interior of the packaging container.

6. The oxygen indicator according to claim 1, wherein a second self-adhesive layer is provided on a second opposite surface of said substrate to the first surface thereof.

7. The oxygen indicator according to claim 6, wherein a first release member is provided on the second self-adhesive layer.

8. An oxygen indicator web comprising:
   a plurality of the oxygen indicators, each oxygen indicator as defined in claim 1,
   wherein said oxygen indicating member and the single-sided self-adhesive plastic member are formed in a strip shape.

9. The oxygen indicator web according to claim 8, wherein spots of said oxygen indicator composition are fixed at regular intervals to the first surface of said substrate and the respective spots of oxygen indicator composition are adhered to the self-adhesive layer.

10. A method for manufacturing a deoxidizer package strip with an oxygen indicating function, comprising the step of pasting the oxygen indicator web stated in claim 8, continuously to a packaged deoxidizer strip.

11. A method for manufacturing a deoxidizer package with an oxygen indicating function, comprising the steps of:
    pasting the oxygen indicator web as stated in claim 8, continuously to a packaged deoxidizer strip which comprises a plurality of deoxidizer packages, thereby forming a strip of deoxidizer packages; and
    cutting the strip of deoxidizer packages to separate the individual deoxidizer packages having the oxygen indicator.

12. The oxygen indicator web according to claim 8, wherein the width of said single-sided self-adhesive member is wider than that of said oxygen indicating member and said oxygen indicating member is provided at an approximate center position in the width direction of said single-sided self-adhesive member.

13. The deoxidizer package with an oxygen indicating function, wherein the oxygen indicator as stated in claim 12, is provided by the single-sided self-adhesive member pasted in a manner that the oxygen indicator encloses a the seal portion of the deoxidizer package.

14. The oxygen indicator web according to claim 8, wherein a third self-adhesive layer is provided on a second opposite surface of said substrate to the first surface thereof.

15. The oxygen indicator web according to claim 14, wherein a second release member is provided on the third self-adhesive layer.

16. The deoxidizer package with an oxygen indicating function, wherein the oxygen indicator as stated in claim 14, is provided by the single-sided self-adhesive member pasted in a manner that the oxygen indicator encloses a seal portion of the deoxidizer package.

17. The oxygen indicator according to claim 1, wherein said single-sided self-adhesive plastic member consists of oriented polypropylene or polyester.

18. The oxygen indicator according to claim 1, wherein an overprint agent is printed on said oxygen indicator composition.

* * * * *

UNITED STATES PATENT AND TRADEMARK OFFICE
CERTIFICATE OF CORRECTION

PATENT NO. : 6,676,901 B1
DATED : January 13, 2004
INVENTOR(S) : Hidetoshi Hatakeyama et al.

It is certified that error appears in the above-identified patent and that said Letters Patent is hereby corrected as shown below:

<u>Title page, Item [54] and Column 1, line 1,</u>
Title, delete "OXYGEN INDICATOR PACKAGE EQUIPPED...." insert
-- OXYGEN INDICATOR, PACKAGE EQUIPPED... --.

Signed and Sealed this

Eighteenth Day of May, 2004

JON W. DUDAS
*Acting Director of the United States Patent and Trademark Office*